(12) United States Patent
Ye et al.

(10) Patent No.: US 6,875,906 B1
(45) Date of Patent: Apr. 5, 2005

(54) CONTROL OF SPOROCYTE OR MEIOCYTE FORMATION IN PLANTS

(75) Inventors: De Ye, Singapore (SG); Wei-Cai Yang, Singapore (SG); Venkatesan Sundaresan, Singapore (SG); Jian Xu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 09/701,023

(22) PCT Filed: Mar. 22, 1999

(86) PCT No.: PCT/SG99/00023

§ 371 (c)(1),
(2), (4) Date: Jun. 18, 2001

(87) PCT Pub. No.: WO00/56907

PCT Pub. Date: Sep. 28, 2000

(51) Int. Cl.$^7$ ................. C12N 15/29; C12N 15/82; C12N 15/10; A01H 5/00; A01H 1/02
(52) U.S. Cl. ................. 800/278; 800/286; 800/290; 435/419; 536/23.6; 536/24.5
(58) Field of Search ................. 800/278, 286, 800/290, 271, 274, 303; 435/419, 468; 536/23.6, 24.5

(56) References Cited

U.S. PATENT DOCUMENTS

| 5,034,323 A | 7/1991 | Jorgensen et al. |
| 5,283,184 A | 2/1994 | Jorgensen et al. |

OTHER PUBLICATIONS

Aarts et al. Nature 363:715–717, Jun. 1993.*
Elliott et al. Plant Cell 8:155–168, Feb. 1995.*
Yang et al. Genes Devel. 13:2108–2117, 1999.*
Kakavas et al. Accession No. AF016585 Jul. 1997.*
Reicher et al. Accession No. 081836, Jun. 1998.*
Rounsley et al. Accession No. B98482, 1997.*
Schiefhaler et al. Proc. Natl. Acad. Sci USA 96(20):11664–11669, 1999.*
Matsuoka et al. Plant Cell 5:1039–1048, Sep. 1993.*
Spielman et al. Development 124(13):2645–2657, 1997.*
Weigel et al. Cell 69:843–859, May 1992.*
Pnueli et al. Plant Cell 6(2):163–173, Feb. 1994.*
Rounsley et al. Accession No. B67977 published Dec. 9, 1997.*
Meinke et al. Science 282: 662–682 (Oct. 1998).*
Bowman, J.L. pp. 1–7 In: Encyclopedia of Life Sciences, Nature Publishing Group (2001).*
Somerville et al. pp. 1–6 In: Arabidopsis, Meyerowitz et al, eds., Cold Spring Harbor Laboratory Press: Plainview, NY (1994).*
Aarts, Mark G.M., et al., "Transposon Tagging of a Male Sterility Gene in Arabidopsis," *Nature* 363(6431): 715–717, Jun. 24, 1993.
Drews, Gary N., et al., "Genetic Analysis of Female Gametophyte Development and Function," *The Plant Cell* 10: 5–17, Jan. 1998.
Elliott, Robert C., et al., "Aintegumenta, An APETALA2–like Gene of Arabidopsis With Pleiotropic Roles in Ovule Development and Floral Organ Growth," *The Plant Cell* 8(2): 155–168, Feb. 1996.
Kakavas, S.J., et al., "*Streptomyces caelestis* cytochrome P–450 Hydroxylase Homolog (nidi) Gene," DATABASE EMBL [Online] EBI, Accession No. AF016585, Dec. 7, 1997.
Smyth, David R., et al., "Early Flower Development in Arabidopsis," *The Plant Cell* 2:755–767, Aug. 1990.
Yang, W.C., et al., "The Sporocyteless Gene of Arabidopsis Is Required for Initiation of Sporogenesis and Encodes a Novel Nuclear Protein," *Genes and Development* 13(16): 2108–2117, Aug. 15, 1999.

* cited by examiner

Primary Examiner—David T. Fox
(74) Attorney, Agent, or Firm—Rothwell, Figg, Ernst & Manbeck

(57) ABSTRACT

The present invention provides genes and encoded proteins that are involved in meiocyte formation during the growth of plants. The transformation of plants and plant-related hosts with these genes in altered or unaltered form, or the mutation of these genes in endogenous form, renders a plant capable during growth of bearing seedless fruits and/or pollenless flowers. The invention further provides methods of producing transgenic plants which are capable of bearing seedless fruits and/or pollenless flowers.

10 Claims, 7 Drawing Sheets

5' of the SPL gene gtagcatcga tctctaacaa cgctacccgt ttacccgtac cggtagaccc gggtgttgt 59

3' of Ds element
gcta<<<cagggat gaaaacggtc ggtaacggtc ggtaaaatac------------------
------------------Ds element------------------------------------
tacgggattt ttcccatcct actttcatcc cgg>>>gctacaa ggcttcccaa
              5' of Ds element gctcatcggg agcaacagga tctattgtgg tggagtcggg tcgggtcagg ttatgatcga
cccggttatt tctccatggg gttttgttga gacctcctcc actactcatg agctctcttc a

FIG. 1A.

cagggat gaaaacggtc ggtaacggtc ggtaaaatac tacgggattt ttcccatcct
actttcatcc cgg

FIG. 1B.

```
CAGACTTAAAGCTTTCGTCTTTACCTCTTCCCTTCTCTCTCTCTATCTAAAAAGAGTTCCGACA      64
AGAAGATCATCATCAATGGCGACTTCTCTCTTCTTCATGTCAACAGATCAAAACTCCGTCGGAA     120
ACCCAAACGATCTTCTGAGAAACACCCGTCTTGTCGTCAATAGCTCCGGCGAGATCCGGACAGA     192
GACACTGAAGAGTCGTGGTCGGAAACCAGGATCGAAGACAGGTCAGCAAAAACAGAAGAAACCA     256
ACGTTGAGAGGAATGGGTGTAGCAAAGCTCGAGCGTCAGAGAATCGAAGAAGAAAAGAAGCAAC     320
TCGCCGCCGCCACAGTCGGAGACACGTCATCAGTAGCATCGATCTCTAACAACGCTACCCGTTT     384
ACCCGTACCGGTAGACCCGGGTGTTGTGCTACAAGGCTTCCCAAGCTCACTCGGGAGCAACAGG     448
ATCTATTGTGGTGGAGTCGGGTCGGGTCAGGTTATGATCGACCCGGTTATTTCTCCATGGGGTT     512
TTGTTGAGACCTCCTCCACTACTCATGAGCTCTCTTCAATCTCAAATCCTCAAATGTTTAACGC     576
TTCTTCCAATAATCGCTGTGACACTTGCTTCAAGAAGAAACGTTTGGATGGTGATCAGAATAAT     640
GTAGTTCGATCCAACGGTGGTGGATTTTCGAAATACACAATGATTCCTCCTCCGATGAACGGCT     704
ACGATCAGTATCTTCTTCAATCAGATCATCATCAGAGGAGCCAAGGTTTCCTTTATGATCATAG     768
AATCGCTAGAGCAGCTTCAGTTTCTGCTTCTAGTACTACTATTAATCCTTATTTCAACGAGGCA     832
ACAAATCATACGGGACCAATGGAGGAATTTGGGAGCTACATGGAAGGAAACCCTAGAAATGGAT     896
CAGGAGGTGTGAAGGAGTACGAGTTTTTTTCCGGGGAAATATGGTGAAAGAGTTTCAGTGGTGGC    960
TACAACGTCGTCACTCGTAGGTGATTGCAGTCCTAATACCATTGATTTGTCCTTGAAGCTTTAA   1024
ATGTTTTATCTTTCTATATTGATTTAAACAAAATCGTCTCTTTAAAGAAAAAACATTTTAAGTA   1088
GATGAAAGTAAGAAACAGAAGAAAAAAAAGAGAGAGCCTTTTTTGGTGTATGCATCTGAGAGCT   1152
GAGTCGAAAGAAAGATTCAGCTTTTGGATTACCCTTTTGGTTGTTTATTATGAGATTCTAACCT   1216
AAACACTCAGACATATATGTTCTGTTCTCTTCCTTAATTGTTGTCATGAAACTTCTCAAAAAAA   1280
AAAAAAAAAAAAAAAAAAAAAA                                             1302
```

FIG.2

Met Ala Thr Ser Leu Phe Phe Met Ser Thr Asp Gln Asn Ser Val Gly Asn Pro Asn Asp
1          5              10             15             20
Leu Leu Lrg Asn Thr Arg Leu Val Val Asn Ser Ser Gly Glu Ile Arg Thr Glu Thr Leu
         25             30             35             40
Lys Ser Arg Gly Arg Lys Pro Gly Ser Lys Thr Gly Gln Gln Lys Gln Lys Lys Pro Thr
         45             50             55             60
Leu Arg Gly Met Gly Val Ala Lys Leu Glu Arg Gln Arg Ile Glu Glu Glu Lys Lys Gln
         65             70             75             80
Leu Ala Ala Ala Thr Val Gly Asp Thr Ser Ser Val Ala Ser Ile Ser Asn Asn Ala Thr
         85             90             95             100
Arg Leu Pro Val Pro Val Asp Pro Gly Val Val Leu Gln Gly Phe Pro Ser Ser Leu Gly
         105            110            115            120
Ser Asn Arg Ile Tyr Cys Gly Gly Val Gly Ser Gly Gln Val Met Ile Asp Pro Val Ile
         125            130            135            140
Ser Pro Trp Gly Phe Val Glu Thr Ser Ser Thr Thr His Glu Leu Ser Ser Ile Ser Asn
         145            150            155            160
Pro Gln Met Phe Asn Ala Ser Ser Asn Asn Arg Cys Asp Thr Cys Phe Lys Lys Lys Arg
         165            170            175            180
Leu Asp Gly Asp Gln Asn Asn Val Val Arg Ser Asn Gly Gly Gly Phe Ser Lys Tyr Thr
         185            190            195            200
Met Ile Pro Pro Pro Met Asn Gly Tyr Asp Gln Tyr Leu Leu Gln Ser Asp His His Gln
         205            210            215            220
Arg Ser Gln Gly Phe Leu Tyr Asp His Arg Ile Ala Arg Ala Ala Ser Val Ser Ala Ser
         225            230            235            240
Ser Thr Thr Ile Asn Pro Tyr Phe Asn Glu Ala Thr Asn His Thr Gly Pro Met Glu Glu
         245            250            255            260
Phe Gly Ser Tyr Met Glu Gly Asn Pro Arg Asn Gly Ser Gly Gly Val Lys Glu Tyr Glu
         265            270            275            280
Phe Phe Pro Gly Lys Tyr Gly Glu Arg Val Ser Val Val Ala Thr Thr Ser Ser Leu Val
         285            290            295            300
Gly Asp Cys Ser Pro Asn Thr Ile Asp Leu Ser Leu Lys Leu
         305            310

FIG. 3

```
AP3         1  MARGKIEIKRIENQTNRQ
DEFA        1  MERGKIEIKRIENQANRQ
AG_         1  SGRGKIEIKRIENTTNRQ
MCM1        1  KERRKIEIKFIENKTRRE
SRF         1  RGRVKIKMEYIDNKLRRY
GLO         1  MGRGKIEIKRIENSSNRQ
RLM1-yeast  1  MGRRKIEIQRISDDRNRA
SMP1-yeast  1  MGRRKIEIEPIKDDRNRT
MEF2D       1  MGRKKIEIQRITDERNRQ
AGL5        1  MGRGKIEIKRIENANSRQ
FBP11       1  MGRGKIEIKRIENNTNRQ
BOAP1       1  MGRGKVGIKRIENKINRQ
AGL11       1  MGRGKIEIKRIENSTNRQ
SPL         1  MGVAKLERQRIEE-KKQ
```

Figure 4

FIGURE 5

-2690
cggatcccaagaatctttctatgcctgcctaaacccagcaatataaatcaaaccttcacacgct
tcggttcttctttacacgtgccggaaaaaaaccctagtagtagccgcccaatgaccatctaaa
gtggtccccgtgatgacacgtgtcagttggaccactatccgtaacttaacatgaaagcacatgt
ggggtccctctttcgtcctttgccctaccagttccttgtcctagcccacaatacaatctacgcg
gtatctatatcaaagtttatctagctattttccgaaatagaaagcatatacttccatttatttt
tgaacaaattaaacttggtagaaataaatctttcgatattgatttatttcgatttagtgtaat
tctattatcatctcgcgtgtcattctaggcttatagcaacagtgtaggtatgttgcaatgttgg
gttggtcatgccgtttggatttatttccagtgattaattcagattttatttttcttcttaatta
tctacgtataacaaaatctcgctaaccgcagagtgaatttgcatgtcactcatgaatgttctga
gtataagaagtgagtaatttgtttataaatatatgaacttatgaagatacatattgaagttgt
tttgtttgggggtaaaaaaggttattgagtgttatatgataactttactcagaaaacgtactt
agcaaaggtaattcgaagtacctttggaatcgagtaaatactgataactagaaaaataagata
cataatggagaaataattaaatatatttgtatttcttttttgtttaacaacgtacgttttatta
ttagctagtatacatttacaacggttacgtagatcatataatagccatttaagatgtacaacat
ctcatctggttacttcatttatataaaaaaaaacgaaatctcaacacatagtaatgtataatt
acttcagtggggcttctcttaagacttgtattgagaatatccatataaaacaaactttgtatta
agataattaaaattttctaatagtaggtattgggctgaagccaagattaacatggaggcagctt
taaaatgtttccttatatgatgcagccatcatttctactctactccgtagctccaaacccttct
cgtaattcacgtctctcatgctattcttttgctttcgtcctcctctcatgtgaagcaataact
atctctcgattttttttcttcaaatacgaaagctaactttttcaaataaatgtcaaatatatta
attttcgttttgtatttagtattttattgtcagctaagtatagtgagttttaagcttaccog
tcgtatctatcatatattcatatacatatcacattagtcaaagtaaataaaaattgttcttga

Figure 5 (cont)

agaaaaaaaaaatacatataactgcgagtctgcgactgtaactggacttgcttattttagttga
tatgagctgagtaaaatcacgttgtcccagaccttgctcgctacaatcggcgaatggtctaacg
tcccgacacctgtcctcgatccgcgggtactatattctttgcaatgtgatgcacgcgctgttac
tattggacagtgtttctcacctcacgactgagcctatgcgagtagcgacaatctccgatttgct
gtctccatggtagggattatcacaatctctgatttttttatcaggaacaagtaaataaatagc
tttgagtttttgttttttttctacattcttcgcccaaaagatgtaagaaaataaaggatttgaa
accttgttctgttgttactcctttaaattcttaaaaactataaatcattatatctttgatctgt
ttcacaaactaatcatattcgttgcaaagtgagaattcgtcccactttactcttacaccgata
ctagtattatagatgtacagcatagtattccatatctagttatttagtcaaaactctatatatt
aagaggtaggttaattaattaaggagtaattgaagattatagaaagaataaaaaataccattta
atggacagaaccaaagataactaactatcatactataatgttgaatttcttccacgatccaatg
catggataacaacatcaatcaaatcatacattcatgctatataacatagttttcagttacaaac
tctcttttttatttatttcagttgttccttttcatgaccatattaacatcaaataatgcatttt
tttcaacgtctcttgacttacacccactaatattgacaaattgaacatctatacgactatacac
acataagttaaaaatgcatgcaagtgctaagggaatttataacatctaaggttaataagactaa
gaaagtataaaataagaatacgtattatgaatttatgatatactttactaatcttttttgaaaaa
tactttaattaatctactataggggtaaaaagtaaaaagaaataaagatacgtttatccgc
atatagtacctggaaataacagaaaataaaaacacaggtaagtactttgcctgagctagtatat
gaacactaaagagatacacacacacaaaaagagagcagaaacaaaacacacacacacttaaagctt
tcgtctttacctc

+1 ttcccttctctctctctatctaaaaagagttccgagaagaagatcatcatcaatgggogacttct
ctcttcttcatgtcaacagatcaaaactccgtcggaaacccaaacgatcttctgagaaacacc
gtcttgtcgtcaacagctccggcgagatccggacagagacactgaagagtcgtggtcggaaacc
aggatcgaagacaggtcagcaaaaacagaagaaaccaacgttgagaggaatgggtgtagcaaag
ctcgagcgtcagagaatcgaagaagaaaagaagcaactcgccgocgccacagtcggagacacgt
catcagtagcatcgatctctaacaacgctacccgtttacccgtaccggtagaccgggtgttgt
gctacaaggcttcccaagctcactcgggagcaacaggatctattgtggtggagtcgggtcgggt
caggttatgatcgacccggttatttctccatgggtttttgttgagacctcctccactactcatg
agctctcttcaatctcaaatcctcaaatgtttaaogcttcttccaataatcgctgtgacacttg
cttcaaggtttgtttgttttttaatcgttttcatcaacatgattgatatatatagtttttgc
acttgaaaaagctttgattcttatttatgtaaaaaactgcagaagaaacgtttggatggtgatc

Figure 5 (cont)

agaataatgtagttcgatccaacggtggtggatttccgaaatacacaatgattcctcctccgat
gaacggctacgatcagtatcttcttcaatcagatcatcatcagaggagccaaggtttcctttat
gatcatagaatcgctagagcagcttcagtttctgcttctagtactactattaatccttatttca
acgaggcaacaaatcatacggtactaagtatagtccatttattaatactcatatataggtatat
atgtatataactgttgatcttattgatttaactggtgggcttagggaccaatggaggaattg
ggagctacatggaaggaaaccctagaaatggatcaggaggtgtgaaggagtacgagtttttcc
ggggaaatatggtgaaagagtttcagtggtggctaaaacgtcgtcactcgtaggtgattgcagt
cctaataccattgatttgtccttgaagctttaaatgttttatctttctatattgatttaaacaa
aatcgtctctttaaagaaaaaacattttaagtagatgaaagtaagaaacagaagaaaaaaaga
gagagccttttttggtgtatgcatctgagagctgagtcgaaagaaagattcagcttttggatta
ccctttttggttgtttattatgagattctaacctaaacactcagacatatatgttctgttctctt
ccttaattgttgtcatgaaacttctc

SEQUENCE LISTING

<160> NUMBER OF SEQ ID NOS: 20

<210> SEQ ID NO 1
<211> LENGTH: 1302
<212> TYPE: DNA
<213> ORGANISM: Arabidopsis thaliana

<400> SEQUENCE: 1

| | | | | | |
|---|---|---|---|---|---|
| cacacttaaa | gctttcgtct | ttacctcttc | ccttctctct | ctctatctaa | aaagagttcc | 60 |
| gagaagaaga | tcatcatcaa | tggcgacttc | tctcttcttc | atgtcaacag | atcaaaactc | 120 |
| cgtcggaaac | ccaaacgatc | ttctgagaaa | cacccgtctt | gtcgtcaata | gctccggcga | 180 |
| gatccggaca | gagacactga | agagtcgtgg | tcggaaacca | ggatcgaaga | caggtcagca | 240 |
| aaaacagaag | aaaccaacgt | tgagaggaat | gggtgtagca | aagctcgagc | gtcagagaat | 300 |
| cgaagaagaa | aagaagcaac | tcgccgccgc | cacagtcgga | gacacgtcat | cagtagcatc | 360 |
| gatctctaac | aacgctaccc | gtttaccccgt | accggtagac | ccgggtgttg | tgctacaagg | 420 |
| cttcccaagc | tcactcggga | gcaacaggat | ctattgtggt | ggagtcgggt | cgggtcaggt | 480 |
| tatgatcgac | ccggttattt | ctccatgggg | ttttgttgag | acctcctcca | ctactcatga | 540 |
| gctctcttca | atctcaaatc | ctcaaatgtt | taacgcttct | tccaataatc | gctgtgacac | 600 |
| ttgcttcaag | aagaaacgtt | tggatggtga | tcagaataat | gtagttcgat | ccaacggtgg | 660 |
| tggattttcg | aaatacacaa | tgattcctcc | tccgatgaac | ggctacgatc | agtatcttct | 720 |
| tcaatcagat | catcatcaga | ggagccaagg | tttcctttat | gatcatagaa | tcgctagagc | 780 |
| agcttcagtt | tctgcttcta | gtactactat | taatccttat | ttcaacgagg | caacaaatca | 840 |
| tacgggacca | atggaggaat | tgggagcta | catggaagga | aaccctagaa | atggatcagg | 900 |
| aggtgtgaag | gagtacgagt | tttttccggg | gaaatatggt | gaaagagttt | cagtggtggc | 960 |
| tacaacgtcg | tcactcgtag | gtgattgcag | tcctaatacc | attgatttgt | ccttgaagct | 1020 |
| ttaaatgttt | tatctttcta | tattgattta | acaaaatcg | tctctttaaa | gaaaaaacat | 1080 |
| tttaagtaga | tgaaagtaag | aaacagaaga | aaaaaagag | agagcctttt | ttggtgtatg | 1140 |
| catctgagag | ctgagtcgaa | agaaagattc | agcttttgga | ttacccttt | ggttgtttat | 1200 |
| tatgagattc | taacctaaac | actcagacat | atatgttctg | ttctcttcct | taattgttgt | 1260 |
| catgaaactt | ctcaaaaaaa | aaaaaaaaaa | aaaaaaaaaa | aa | | 1302 |

<210> SEQ ID NO 2
<211> LENGTH: 271
<212> TYPE: DNA
<213> ORGANISM: Arabidopsis thaliana

<400> SEQUENCE: 2

| | | | | | |
|---|---|---|---|---|---|
| gtagcatcga | tctctaacaa | cgctacccgt | ttacccgtac | cggtagaccc | gggtgttgtg | 60 |
| ctacagggat | gaaaacggtc | ggtaacggtc | ggtaaaatac | tacgggatttt | ttcccatcct | 120 |
| actttcatcc | cgggctacaa | ggcttcccaa | gctcatcggg | agcaacagga | tctattgtgg | 180 |
| tggagtcggg | tcgggtcagg | ttatgatcga | cccggttatt | tctccatggg | gttttgttga | 240 |
| gacctcctcc | actactcatg | agctctcttc | a | | | 271 |

<210> SEQ ID NO 3
<211> LENGTH: 70
<212> TYPE: DNA
<213> ORGANISM: Arabidopsis thaliana -continued

<400> SEQUENCE: 3
cagggatgaa aacggtcggt aacggtcggt aaaatactac gggattttc ccatcctact      60 ttcatcccgg                                                            70

<210> SEQ ID NO 4
<211> LENGTH: 314
<212> TYPE: PRT
<213> ORGANISM: Arabidopsis thaliana

<400> SEQUENCE: 4

Met Ala Thr Ser Leu Phe Phe Met Ser Thr Asp Gln Asn Ser Val Gly
1               5                   10                  15

Asn Pro Asn Asp Leu Leu Arg Asn Thr Arg Leu Val Val Asn Ser Ser
            20                  25                  30

Gly Glu Ile Arg Thr Glu Thr Leu Lys Ser Arg Gly Arg Lys Pro Gly
        35                  40                  45

Ser Lys Thr Gly Gln Gln Lys Gln Lys Pro Thr Leu Arg Gly Met
    50                  55                  60

Gly Val Ala Lys Leu Glu Arg Gln Arg Ile Glu Glu Lys Lys Gln
65                  70                  75                  80

Leu Ala Ala Ala Thr Val Gly Asp Thr Ser Ser Val Ala Ser Ile Ser
                85                  90                  95

Asn Asn Ala Thr Arg Leu Pro Val Pro Val Asp Pro Gly Val Val Leu
            100                 105                 110

Gln Gly Phe Pro Ser Ser Leu Gly Ser Asn Arg Ile Tyr Cys Gly Gly
        115                 120                 125

Val Gly Ser Gly Gln Val Met Ile Asp Pro Val Ile Ser Pro Trp Gly
    130                 135                 140

Phe Val Glu Thr Ser Ser Thr Thr His Glu Leu Ser Ser Ile Ser Asn
145                 150                 155                 160

Pro Gln Met Phe Asn Ala Ser Ser Asn Asn Arg Cys Asp Thr Cys Phe
                165                 170                 175

Lys Lys Lys Arg Leu Asp Gly Asp Gln Asn Asn Val Val Arg Ser Asn
            180                 185                 190

Gly Gly Gly Phe Ser Lys Tyr Thr Met Ile Pro Pro Met Asn Gly
        195                 200                 205

Tyr Asp Gln Tyr Leu Leu Gln Ser Asp His His Gln Arg Ser Gln Gly
    210                 215                 220

Phe Leu Tyr Asp His Arg Ile Ala Arg Ala Ala Ser Val Ser Ala Ser
225                 230                 235                 240

Ser Thr Thr Ile Asn Pro Tyr Phe Asn Glu Ala Thr Asn His Thr Gly
                245                 250                 255

Pro Met Glu Glu Phe Gly Ser Tyr Met Glu Gly Asn Pro Arg Asn Gly
            260                 265                 270

Ser Gly Gly Val Lys Glu Tyr Glu Phe Phe Pro Gly Lys Tyr Gly Glu
        275                 280                 285

Arg Val Ser Val Val Ala Thr Thr Ser Ser Leu Val Gly Asp Cys Ser
    290                 295                 300

Pro Asn Thr Ile Asp Leu Ser Leu Lys Leu
305                 310

<210> SEQ ID NO 5
<211> LENGTH: 18
<212> TYPE: PRT

```
<213> ORGANISM: Arabidopsis thaliana and Anthirrhinum sp.

<400> SEQUENCE: 5

Met Ala Arg Gly Lys Ile Gln Ile Lys Arg Ile Glu Asn Gln Thr Asn
1               5                   10                  15

Arg Gln

<210> SEQ ID NO 6
<211> LENGTH: 18
<212> TYPE: PRT
<213> ORGANISM: Arabidopsis thaliana

<400> SEQUENCE: 6

Ser Gly Arg Gly Lys Ile Glu Ile Lys Arg Ile Glu Asn Thr Thr Asn
1               5                   10                  15

Arg Gln

<210> SEQ ID NO 7
<211> LENGTH: 18
<212> TYPE: PRT
<213> ORGANISM: Yeast sp.

<400> SEQUENCE: 7

Lys Glu Arg Arg Lys Ile Glu Ile Lys Phe Ile Glu Asn Lys Thr Arg
1               5                   10                  15

Arg His

<210> SEQ ID NO 8
<211> LENGTH: 18
<212> TYPE: PRT
<213> ORGANISM: Homo sapiens

<400> SEQUENCE: 8

Arg Gly Arg Val Lys Ile Lys Met Glu Phe Ile Asp Asn Lys Leu Arg
1               5                   10                  15

Arg Tyr

<210> SEQ ID NO 9
<211> LENGTH: 18
<212> TYPE: PRT
<213> ORGANISM: Antirrhinum sp.

<400> SEQUENCE: 9

Met Gly Arg Gly Lys Ile Glu Ile Lys Arg Ile Glu Asn Ser Ser Asn
1               5                   10                  15

Arg Gln

<210> SEQ ID NO 10
<211> LENGTH: 18
<212> TYPE: PRT
<213> ORGANISM: Yeast sp.

<400> SEQUENCE: 10

Met Gly Arg Arg Lys Ile Glu Ile Gln Arg Ile Ser Asp Asp Arg Asn
1               5                   10                  15

Arg Ala

<210> SEQ ID NO 11
<211> LENGTH: 18
<212> TYPE: PRT
<213> ORGANISM: Yeast sp.
```

```
<400> SEQUENCE: 11

Met Gly Arg Arg Lys Ile Glu Ile Glu Pro Ile Lys Asp Asp Arg Asn
1               5                   10                  15
Arg Thr

<210> SEQ ID NO 12
<211> LENGTH: 18
<212> TYPE: PRT
<213> ORGANISM: Homo sapiens

<400> SEQUENCE: 12

Met Gly Arg Lys Lys Ile Gln Ile Gln Arg Ile Thr Asp Glu Arg Asn
1               5                   10                  15
Arg Gln

<210> SEQ ID NO 13
<211> LENGTH: 18
<212> TYPE: PRT
<213> ORGANISM: Arabidopsis thaliana

<400> SEQUENCE: 13

Met Gly Arg Gly Lys Ile Glu Ile Lys Arg Ile Glu Asn Ala Asn Ser
1               5                   10                  15
Arg Gln

<210> SEQ ID NO 14
<211> LENGTH: 18
<212> TYPE: PRT
<213> ORGANISM: Petunia

<400> SEQUENCE: 14

Met Gly Arg Gly Lys Ile Glu Ile Lys Arg Ile Glu Asn Asn Thr Asn
1               5                   10                  15
Arg Gln

<210> SEQ ID NO 15
<211> LENGTH: 18
<212> TYPE: PRT
<213> ORGANISM: Brassica oleracea

<400> SEQUENCE: 15

Met Gly Arg Gly Arg Val Gln Leu Lys Arg Ile Glu Asn Lys Ile Asn
1               5                   10                  15
Arg Gln

<210> SEQ ID NO 16
<211> LENGTH: 18
<212> TYPE: PRT
<213> ORGANISM: Arabidopsis thaliana

<400> SEQUENCE: 16

Met Gly Arg Gly Lys Ile Glu Ile Lys Arg Ile Glu Asn Ser Thr Asn
1               5                   10                  15
Arg Gln

<210> SEQ ID NO 17
<211> LENGTH: 17
<212> TYPE: PRT
<213> ORGANISM: Arabidopsis thaliana
```

<400> SEQUENCE: 17

Met Gly Val Ala Lys Leu Glu Arg Gln Arg Ile Glu Glu Glu Lys Lys
1               5                   10                  15
Gln

<210> SEQ ID NO 18
<211> LENGTH: 4071
<212> TYPE: DNA
<213> ORGANISM: Arabidopsis thaliana

<400> SEQUENCE: 18

| | |
|---|---|
| cggatcccaa gaatctttct atgcctgcct aaacccagca atataaatca aaccttcaca | 60 |
| cgcttcggtt cttctttaca cgtgccggaa aaaaaaccct agtagtagcc gcccaatgac | 120 |
| catctaaagt ggtccccgtg atgacacgtg tcagttggac cactatccgt aacttaacat | 180 |
| gaaagcacat gtgggtccc tctttcgtcc tttgccctac cagttccttg tcctagccca | 240 |
| caatacaatc tacgcggtat ctatatcaaa gtttatctag ctattttccg aaatagaaag | 300 |
| catatacttc catttatttt tgaacaaatt aaacttggta gaaataaaat ctttcgatat | 360 |
| tgatttattt cgatttagtg taattctatt atcatctcgc gtgtcattct aggcttatag | 420 |
| caacagtgta ggtatgttgc aatgttgggt tggtcatgcc gtttggattt atttccagtg | 480 |
| attaattcag attttatttt tcttcttaat tatctacgta taacaaaatc tcgctaaccg | 540 |
| cagagtgaat ttgcatgtca ctcatgaatg ttttgagtat aagaagtgag taatttgttt | 600 |
| tataaatata tgaacttatg aagatacata ttgaagttgt tttgtttggg ggtaaaaaag | 660 |
| gttatttgag tgttatatga taactttact cagaaaacgt acttagcaaa ggtaattcga | 720 |
| agtacctttg gaatcgagta aatactgata actagaaaaa ataagataca taatggagaa | 780 |
| ataattaaat atatttgtat ttcttttttg tttaacaacg tacgttttat tattagctag | 840 |
| tatacattta caacggttac gtagatcata taatagccat ttaagatgta caacatctca | 900 |
| tctggttact tcatttatat aaaaaaaaaa cgaaatctca acacatagta atgtataatt | 960 |
| acttcagtgg ggcttctctt aagacttgta ttgagaatat ccatataaaa caaactttgt | 1020 |
| attaagataa ttaaaatttt ctaatagtag gtattgggct gaagccaaga ttaacatgga | 1080 |
| ggcagcttta aaatgtttcc ttatatgatg cagccatcat ttctactcta ctccgtagct | 1140 |
| ccaaaccctt ctcgtaattc acgtctctca tgctattctt tttgctttcg tcctcctctc | 1200 |
| atgtgaagca ataactatct ctcgattttt tttttcaaat accgaaagct aactttttca | 1260 |
| aataaatgtc aaatatatta attttcgttt tgtatttagt attttatttg tcagctaagt | 1320 |
| atagtgagtt tttaagctta ctcgtcgtat ttatcatata ttcatataca tatcacatta | 1380 |
| gtcaaagtaa ataaaattt gtttttgaag aaaaaaaaaa tacatataac tgcgagtctg | 1440 |
| cgactgtaac tggacttgct tattttagtt gatatgagct gagtaaaatc acgttgtccc | 1500 |
| agaccttgct cgctacaatc ggcgaatggt ctaacgtccc gacacctgtc ctcgatccgc | 1560 |
| gggtactata ttcttttgcaa tgtgatgcac gcgctgttac tattggacag tgtttctcac | 1620 |
| ctcacgactg agcctatgcg agtagcgaca atctccgatt tgctgtctcc atggtaggga | 1680 |
| ttatcacaat ctctgatttt ttttatcagg aacaagtaaa taaatagctt tgagtttttg | 1740 |
| ttttttttct acattcttcg cccaaaagat gtaagaaaat aaaggatttg aaaccttgtt | 1800 |
| ctgttgttac tcctttaaat tcttaaaaac tataaatcat tatatctttg atctgtttca | 1860 |
| caaactaatc atattcgttg caaagtgaga attcgtccca ctttactctt tacaccgata | 1920 |

-continued

| | |
|---|---|
| ctagtattat agatgtacag catagtattc catatctagt tatttagtca aaactctata | 1980 |
| tattaagagg taggttaatt aattaaggag taattgaaga ttatagaaag aataaaaaat | 2040 |
| accatttaat ggacagaacc aaagataact aactatcata ctataatgtt gaatttcttc | 2100 |
| cacgatccaa tgcatggata acaacatcaa tcaaatcata cattcatgct atataacata | 2160 |
| gttttcagtt acaaactctc ttttttattt atttcagttg ttccttttca tgaccatatt | 2220 |
| aacatcaaat aatgcatttt tttcaacgtc tcttgactta cacccactaa tattgacaaa | 2280 |
| ttgaacatct atacgactat acacacataa gttaaaaatg catgcaagtg ctaagggaat | 2340 |
| ttataacatc taaggttaat aagactaaga agtataaaa taagaatacg tattatgaat | 2400 |
| ttatgatata ctttactaat cttttttgaaa aatactttaa tttaatctac tataggggt | 2460 |
| aaaaagtaaa aaagaaataa agatacgttt atccgcatat agtacctgga ataacagaa | 2520 |
| aataaaaaca caggtaagta ctttgcctga gctagtatat gaacactaaa gagatacaca | 2580 |
| cacacaaaaa gagagcagaa acaaaacaca cacacttaaa gctttcgtct ttacctcttc | 2640 |
| ccttctctct ctctatctaa aaagagttcc gagaagaaga tcatcatcaa tggcgacttc | 2700 |
| tctcttcttc atgtcaacag atcaaaactc cgtcggaaac ccaaacgatc ttctgagaaa | 2760 |
| cacccgtctt gtcgtcaaca gctccggcga gatccggaca gagacactga agagtcgtgg | 2820 |
| tcggaaacca ggatcgaaga caggtcagca aaaacagaag aaaccaacgt tgagaggaat | 2880 |
| gggtgtagca agctcgagc gtcagagaat cgaagaagaa agaagcaac tcgccgccgc | 2940 |
| cacagtcgga gacacgtcat cagtagcatc gatctctaac aacgctaccc gtttacccgt | 3000 |
| accggtagac ccgggtgttg tgctacaagg cttcccaagc tcactcggga gcaacaggat | 3060 |
| ctattgtggt ggagtcgggt cgggtcaggt tatgatcgac ccggttattt ctccatgggg | 3120 |
| ttttgttgag acctcctcca ctactcatga gctctcttca atctcaaatc ctcaaatgtt | 3180 |
| taacgcttct tccaataatc gctgtgacac ttgcttcaag gtttgtttgt ttttaatcg | 3240 |
| ttttcatcaa catgattgat atatatatag ttttttgcact tgaaaagtt ttgatttta | 3300 |
| tttatgtaaa aaactgcaga agaaacgttt ggatggtgat cagaataatg tagttcgatc | 3360 |
| caacggtggt ggattttcga aatacacaat gattcctcct ccgatgaacg gctacgatca | 3420 |
| gtatcttctt caatcagatc atcatcagag gagccaaggt ttcctttatg atcatagaat | 3480 |
| cgctagagca gcttcagttt ctgcttctag tactactatt aatccttatt tcaacgaggc | 3540 |
| aacaaatcat acggtactaa gtatagtcca tttattaata ctcatatata ggtatatatg | 3600 |
| tatataactg ttgatcttat ttgatttaac tggtgggttt agggaccaat ggaggaattt | 3660 |
| gggagctaca tggaaggaaa ccctagaaat ggatcaggag gtgtgaagga gtacgagttt | 3720 |
| tttccgggga aatatggtga aagagtttca gtggtggcta aaacgtcgtc actcgtaggt | 3780 |
| gattgcagtc ctaataccat tgatttgtcc ttgaagcttt aaatgtttta tctttctata | 3840 |
| ttgatttaaa caaaatcgtc tctttaaaga aaaacatttt taagtagatg aaagtaagaa | 3900 |
| acagaagaaa aaaagagag agcctttttt ggtgtatgca tctgagagct gagtcgaaag | 3960 |
| aaagattcag cttttggatt accctttgg ttgtttatta tgagattcta acctaaacac | 4020 |
| tcagacatat atgttctgtt ctcttcctta attgttgtca tgaaacttct c | 4071 |

<210> SEQ ID NO 19
<211> LENGTH: 24
<212> TYPE: DNA
<213> ORGANISM: Artificial Sequence
<220> FEATURE:
<221> NAME/KEY: misc_feature

```
<222> LOCATION: (1)..(24)
<223> OTHER INFORMATION: primer SPL-Xba-S

<400> SEQUENCE: 19
ctagtctagt ctagaagatc atca                                              24

<210> SEQ ID NO 20
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: primer SPL-BamH1-T

<400> SEQUENCE: 20
cggatccaag cttcaaggac aaatcaatgg t                                      31
```

US 6,875,906 B1

CONTROL OF SPOROCYTE OR MEIOCYTE FORMATION IN PLANTS

This application is a national stage entry of International Application No. PCT/SG99/00023, filed Mar. 22, 1999, designated the U.S.

FIELD OF THE INVENTION

The present invention relates to genes and encoded proteins involved in fertility of plants. More particularly, the present invention relates to the use of genes and encoded proteins involved in meiocyte formation in plants to render plants capable of bearing seedless fruits and/or pollenless flowers.

BACKGROUND OF THE INVENTION

A fundamental part of the life cycle of higher plants is the alternation between a diploid, sporophytic generation and a haploid, gametophytic generation. In flowering plants, the gametophytic generation consists of pollen grains and the embryo sac within the ovary. The transition from the sporophytic phase to the gametophytic phase in higher plants consists of two processes, sporogenesis and gametogenesis. Gametogenesis mainly involves the differentiation of haploid spores into mature gametophytes. See G. N. Drews, et al., *Plant Cell* 10(5) (1988). Sporogenesis is characterized by the differentiation of hypodermal cells in anthers and ovule primordia into archesporial cells that further develop into microsporocytes (pollen mother cells) and megasporocytes (egg mother cells). See J. Bowman, (1994) *Arabidopsis, An Atlas of Morphology and Development*. The microsporocytes and megasporocytes (collectively known as meiocytes) undergo meiosis to produce spores. The formation of meiocytes thus comprises a very important step in plant reproduction.

In *Arabidopsis*, sporogenesis and gametogenesis (also known as megasporogenesis and megagametogenesis, respectively) have been well described. See Bowman, J., 1994, *Arabidopsis, An Atlas of Morphology and Development*. In sporogenesis, bitegmic and tenuinucellate ovules arise as finger-like structures on the placenta in the ovary (carpel) of the plant. A single hypodermal cell at the top of the ovule primordia becomes more prominent than neighboring cells and more conspicuous nucleus, and differentiates into an archesporial cell in stage 10–11 flowers. The archesporial cell then elongates and polarizes its cellular components longitudinally and differentiates into a sporocyte or megaspore mother cell (MMC). The MMC then undergoes meiosis to form four haploid megaspores (tetrad). Shortly after the archesporial cell becomes visible, in stage 11 flowers, the inner and outer integuments form from epidermal cells at the base of the nucellus. In gametogenesis, the outer integument overgrows the inner integument and both inner and outer integuments envelop the nucellus in which the female gametophyte (embryo sac) develops during stage 13. At mature stage, the inner cell layer of the inner integument differentiates into a nutritive endothelium (integumentary tapetum).

Although the above is well known, little is known about the molecular and genetic mechanisms that regulate and control sporogenesis, especially meiocyte formation. The identification of genes that regulate and control meiocyte formation could help understand these mechanisms and find ways to manipulate the fertility of plants.

An object of the present invention thus is to provide isolated nucleic acids and encoded proteins involved in meiocyte formation in plants, which can be used to manipulate plant fertility.

Another object of the present invention is to produce plants in which meiocyte formation has been affected during growth to render the plant capable of bearing altered fruits and/or altered flowers, including seedless fruits and pollenless flowers.

SUMMARY OF THE INVENTION

The present invention relates to the identification of a new gene Sporocyteless (SPL; that is involved in meiocyte formation in both male and female organs in plants. The SPL gene, its encoded polypeptides and proteins, and their homologues, can be utilized to regulate and control meiocyte formation in plants in order to produce altered plants, including plants that are capable of bearing seedless fruits or pollenless flowers, or fruits and flowers which are substantially seedless and pollenless, respectively.

In accordance with one embodiment of the present invention, there are provided isolated nucleic acids and their complements that encode proteins involved in the formation of meiocytes in plants. These isolated nucleic acids include DNA, or portions thereof, of the SPL gene isolated from *Arabidopsis thaliana* ecotype landsberg erecta plant and other plant species. The invention also provides homologues of the SPL gene from *Arabidopsis* and other plant species that can hybridize to DNA of the SPL gene. These homologues demonstrate SPL-type function and can be identified throughout the plant kingdom.

The DNA in accordance with the present invention may exist in various forms, including exogenous DNA that encodes a protein involved in regulating or controlling meiocyte formation in a plant.

The DNA of the present invention also may be exogenous DNA that has been altered by mutation or other means to affect meiocyte formation in a plant. In a preferred embodiment, the present invention provides for the insertion of genetic elements, such as Ds sequences (with or without active Ac sequences) into the above-described nucleic acids.

The present invention further provides for alteration or mutation of a plant's endogenous DNA responsible for meiocyte formation, by direct or targeted mutagenesis, or other technique, which also may affect meiocyte formation. A plant containing the mutated gene thus may be capable of bearing seedless fruits and/or pollenless flowers.

In accordance with the present invention, there are also provided polypeptides or proteins involved in meiocyte formation in plants. These polypeptides or proteins can regulate or control meiocyte formation and include the SPL protein, or portions thereof, of plant origin. SPL proteins from most or all plant species, or homologues of these proteins that demonstrate the same or similar regulatory function (i.e., meiocyte formation) as SPL protein, also are encompassed by this invention. A homologous polypeptide is defined herein as one having an amino acid sequence with at least about 80% or greater homology to the amino acid sequence drawn in FIG. 3 [SEQ ID NO:4].

In another respect, this invention relates to antibodies that bind the polypeptides and proteins described herein. Such antibodies may be used to localize sites of regulatory activity in plants. In accordance with another embodiment of the invention, fusion proteins comprising the SPL protein and an additional peptide, such as a protein tag, also can be used to detect sites of SPL protein/protein interaction in plants.

The present invention further provides isolated nucleic acids and their complements useful as hybridization probes for detecting homologous nucleic acids which are involved in meiocyte formation in plants.

The present invention further provides plants and plant-related hosts, including seeds, plant tissue culture, and plant parts, containing DNA which may be altered or unaltered exogenous DNA, or altered endogenous DNA, or portions thereof, which in many ways may be capable of affecting meiocyte formation during plant growth.

In a further embodiment of the present invention, there are provided methods for producing transgenic plants in which meiocyte formation is affected or controlled, and more particularly methods for producing transgenic plants that are capable of bearing seedless fruits and/or pollenless flowers.

The invention further provides the promoter of the SPL gene which can be used to drive the expression of the SPL gene or a foreign gene in microsporocytes and megasporocytes of plants. The promoter can be used to permit expression of transgene in the reproductive cells of the plant so as to render the plant sterile. The promoter also can be used to express certain genes so as to result in the next generation of seeds from the plant having an altered DNA structure from that of the parent plant.

BRIEF DESCRIPTION OF THE FIGURES AND SEQUENCE LISTING

FIG. 1A [SEQ ID NO:2] shows a portion of the genomic sequence of the SPL gene immediately flanking the Ds sequence (indicated by bold letters). Insertion of the Ds sequence causes a 4 base pair duplication (indicated by underlining) at the insertion site.

FIG. 1B [SEQ ID NO:3] shows the Ds sequence, as shown in FIG. 1A [SEQ ID NO:2].

FIG. 2 [SEQ ID NO:1] shows the cDNA sequence of the SPL gene. The codons in bold, atg and taa, indicate the start and stop codons, respectively, of the open reading frame. The underlined sequence, gcta, indicates the insertion site of the Ds sequence.

FIG. 3 [SEQ ID NO:4] shows the amino acid sequence of the SPL, polypeptide, as deduced from the DNA sequence of FIG. 2 [SEQ ID NO:1]. The codons Val Leu (in bold) are located at the insertion site of the Ds sequence.

FIG. 4 [SEQ. ID NOs:5–17] (AP3, SEQ ID NO:5; DEFA, SEQ ID NO:5; AG_, SEQ ID NO:6; MCM1, SEQ ID NO:7; SRF, SEQ ID NO:8; GLO, SEQ ID NO:9; RLM1-yeast, SEQ ID NO:10; SMP1-yeast, SEQ ID NO:11; MEF2D, SEQ ID NO:12; AGL5, SEQ ID NO:13; FBP11, SEQ ID NO:14; BOAP1, SEQ ID NO:15; AGLI1, SEQ ID NO:16; SPL, SEQ ID NO:17) illustrates the alignment of the first 18 amino acids of the MADS domains from several MADS box transcription factors with amino acids 64 to 80 of the SPL protein.

FIG. 5 [SEQ. ID NO:18] shows the DNA sequence of the promoter of the SPL gene and the coding region of the gene. The promoter sequence begins 2690 nucleotides upstream of the start codon of the SPL gene. The first nucleotide of the start ATG codon is designated as position +1. The start codon ATG and the stop codon TAA are underlined, and two exons are shown in bold.

DETAILED DESCRIPTION OF THE INVENTION

As stated above, the present invention provides isolated nucleic acid molecules (e.g., DNA or RNA) that encode proteins which are involved in, and may be essential to, the formation of meiocytes in the male and female organs of plants. The nucleic acid molecules described herein are useful for producing Sporocyteless (SPL) proteins and SPL-type proteins of plant origin when such nucleic acids are incorporated into any of a variety of protein expression systems known to those skilled in the art. An isolated SPL gene in accordance with the present invention is shown in FIG. 2 [SEQ ID NO:1]. The sequence of the promoter region of the SPL gene, as well as the coding region of the gene is shown in FIG. 5 [SEQ. ID NO:18].

An "isolated" or "substantially pure" nucleic acid (e.g., an RNA, DNA or mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

The term "SPL" represents the wild type form, while "spl" represents the mutated form of a SPL gene. The term "SPL" (no italics) represents the wild type form of the protein described herein.

As used herein, a "portion" or "fragment" of the SPL gene is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from FIGS. 1A [SEQ ID NO:2] or 2 [SEQ ID NO:1], its complement or functionally equivalent nucleic acid sequences. The present invention does not include nucleic acids which exist in the prior art. That is, the present invention includes all nucleic acids having at least 8 nucleotides derived from FIGS. 1A [SEQ ID NO:2] or 2 [SEQ ID NO:1] with the proviso that it does not include nucleic acids existing in the prior art.

The SPL gene according to an embodiment of the present invention can be derived from a dicotyledon, *Arabidopsis thaliana*. The polypeptide encoded by this gene can regulate or control, and may be necessary for, meiocyte formation in a plant. By mutating the SPL gene, a plant becomes unable or less able to produce spores, embryo sac and pollen grain. Therefore, the isolated SPL gene of the present invention can be used to generate modified plants, including plants that produce seedless fruits, pollenless flowers and/or have a larger biomass.

The present invention provides isolated nucleic acids or their complements encoding a protein involved in meiocyte formation, wherein said nucleic acids include: (a) DNA encoding the amino acid sequence set forth in FIG. 3 [SEQ ID NO:4], or (b) naturally occurring DNA, or DNA degenerate to the naturally occurring DNA, that hybridizes to the DNA of (a) under moderately stringent conditions, wherein the naturally occurring DNA has at least 70% identity to the DNA of (a), and wherein said naturally occurring DNA encodes protein involved in meiocyte formation.

The present invention further comprises isolated nucleic acids or their complements encoding a protein involved in meiocyte formation in plants, wherein the nucleic acids comprise naturally occurring DNA, or DNA degenerate to the naturally occurring DNA, from plants that hybridize to the DNA of (a) FIG. 1A [SEQ ID NO:2], or a portion thereof, or (b) FIG. 2 [SEQ ID NO:1], or a portion thereof, under moderately stringent conditions, wherein the naturally occurring DNA has at least about 70% identity to the DNA of (a) or (b), and wherein the naturally occurring DNA encodes such protein.

The present invention further provides isolated nucleic acids or their complements having at least about 70% identity to (a) nucleotides 81–1024 of FIG. 2 [SEQ ID NO:1], or a portion thereof, or (b) variations of (a) which encode the same amino acid sequence as encoded by (a), but employ different codons for some of the amino acids, and wherein the nucleic acids encode a protein involved in meiocyte formation in plants.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target DNA can be readily varied by those skilled in the art.

As used herein, the phrase "moderately stringent" hybridization refers to conditions that permit target DNA to bind a complementary nucleic acid that has about 60%, preferably about 70%, more preferably about 75%, even more preferably about 85% homology to the target DNA; with greater than about 90% homology to target DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

The terms "homology" or "homologue," or to say that a nucleic acid or fragment thereof is "homologous" to another nucleic acid, means that when optimally aligned (with appropriate nucleotide insertions or deletions) with the other nucleic acid (or its complementary strand), there is nucleotide sequence identity in at least about 50% of the nucleotide bases, usually at least about 70%, more usually at least about 80%, preferably at least about 90%, and more preferably at least about 95–98% of the nucleotide bases.

To determine homology between two different nucleic acids, the percent homology may be determined using the BLASTN program "BLAST 2 sequences." This program is available for public use from the National Center for Biotechnology Information (NCBI) over the Internet (http://www.ncbi.nlm.nih.gov/gorf/b12.html) (Altschul et al., 1997). The parameters to be used include the combination of the following parameters which yields the highest calculated percent homology (as calculated below with the default parameters shown in parentheses):

Program—blastn
Matrix—BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, the BLASTN program shows a percent identity across the complete strands or across regions of the two nucleic acids being matched. The program shows as part of the results an alignment and identity of the two strands being compared. If the strands are of equal length, the identity will be calculated across the complete length of the nucleic acids. If the strands are of unequal lengths, the length of the shorter nucleic acid is to be used. If the nucleic acids are similar across only a portion of their sequences, the BLASTN program will show an identity across only these similar portions, which are reported individually. For purposes of determining homology herein, the percent homology refers to the shorter of the two sequences being compared. If any one region is shown in different alignments with differing percent identities, the alignments which yield the greatest homology are to be used.

Alternatively, "homology" exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See Kanehisa, 1984, *Nucl. Acids Res.* 12:203–13. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1969, *J. Mol. Biol.* 31:349–70.

Probe sequences may also hybridize specifically to duplex DNA under certain conditions to form triplex or other higher order DNA complexes. The preparation of such probes and suitable hybridization conditions are well known in the art.

The SPL nucleic acid may be that shown in FIG. 2 [SEQ ID NO:1] or it may be an allele or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in FIG. 2 [SEQ ID NO:1], yet encode a polypeptide with the same amino acid sequence as shown in FIG. 3 [SEQ ID NO:4]. That is, nucleic acids of the present invention include sequences which are degenerate as a result of the genetic code. On the other hand, the encoded polypeptide may comprise an amino acid sequence which differs by one or more amino acid residues from the amino acid sequence shown in FIG. 3 [SEQ ID NO:4]. Nucleic acid encoding a polypeptide which is an amino acid sequence variant, derivative or allele of the amino acid sequence shown in FIG. 3 [SEQ ID NO:4] is also provided by the present invention.

The SPL gene also refers to (a) any DNA sequence that (i) hybridizes to the complement of the DNA sequences that encode the amino acid sequence set forth in FIG. 3 [SEQ ID NO:4] under highly stringent conditions (See Ausubel et al., 1992, Current Protocols in Molecular Biology, (John Wiley and Sons, New York, N.Y.)) and (ii) encodes a gene product functionally equivalent to SPL protein, or (b) any DNA sequence that (i) hybridizes to the complement of the DNA sequences that encode the amino acid sequence set forth in FIG. 3 [SEQ ID NO:4] under less stringent conditions, such as moderately stringent conditions (Ausubel et al., 1992) and (ii) encodes a gene product functionally equivalent to SPL protein. The invention also includes nucleic acid molecules that are the complements of the sequences described herein.

In accordance with a preferred embodiment of the present invention, there is provided an isolated nucleic acid or its complement comprising the same contiguous nucleotide sequence as set forth in FIG. 2 [SEQ ID NO:1], or a portion thereof, which encodes a protein involved in meiocyte formation in plants.

There also is provided an isolated nucleic acid sequence or its complement or which hybridizes to said sequence which comprises the contiguous nucleotide sequence as set forth in FIG. 2 [SEQ ID NO:1] or a portion thereof which is preceded by a nucleic acid sequence which provides the promoter region of the gene. A nucleotide sequence which provides the promoter region is shown in FIG. 5 [SEQ ID NO:18]. Specifically, the promoter comprises the sequence located within nucleotide positions −2690 to −1 of the sequence set forth in FIG. 5 [SEQ ID NO:18], or functional fragments thereof capable of regulating expression of an operably linked gene.

In one embodiment of this invention, the isolated SPL promoter can be operably linked to, and control the expression of, foreign genes.

In accordance with another preferred embodiment of the present invention, there is provided an isolated nucleic acid or its complement comprising the same contiguous nucleotide sequence as set forth in nucleotides 81–1024 of FIG. 2 [SEQ ID NO:1], or a portion thereof, which encodes a protein involved in meiocyte formation in plants.

In accordance with another preferred embodiment of the present invention, there are provided isolated nucleic acids and their complements encoding polypeptides and proteins that are involved in meiocyte formation in plants. Such involvement may include regulating or controlling meiocyte formation. The polypeptides and proteins encoded by the isolated nucleic acids comprise an amino acid sequence having at least about 80%, more preferably about 90% amino acid identity to the reference amino acid sequence in FIG. 3 [SEQ ID NO:4]; with greater than about 95% amino acid sequence identity being especially preferred. In a preferred embodiment, the invention provides an isolated nucleic acid and its complement comprising a nucleic acid encoding a protein which comprises the same amino acid sequence as set forth in FIG. 3 [SEQ ID NO:4].

The SPL polypeptide of the invention thus may be that shown in FIG. 3 [SEQ ID NO:4] which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the SPL polypeptide. Such polypeptides may have an amino acid sequence which differs from that set forth in FIG. 3 [SEQ ID NO:4] by one or more of addition, substitution, deletion or insertion of one or more amino acids.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the SPL polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydrophobic index of amino acids may be considered. The importance of the hydrophobic amino Al acid index in conferring interactive biological function on a protein is generally understood in the art. See Kyte and Doolittle, 1982, J. Mol. Biol. 157:105–32. Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

In another embodiment of the present invention, there is provided isolated DNA molecules comprising DNA having at least eight consecutive nucleotides of bases 81–1024 of FIG. 2 (SEQ ID NO:1], or a complement thereof. In a more preferred embodiment of the invention, the isolated DNA molecule has at least 15 consecutive nucleotides of bases 81–1024 of FIG. 2 [SEQ ID NO:1].

In accordance with another embodiment of the invention, there is provided isolated nucleic acids, or their complements, comprising nucleic acid coding for a mutant SPL polypeptide which blocks, reduces or increases the formation of meiocytes in a plant.

In accordance with another embodiment of the present invention, there is provided a method for the recombinant production of SPL and SPL-type proteins by expressing the above-described nucleic acid sequences in suitable host cells. The proteins can be expressed under the control of the promoter of the SPL gene.

In another embodiment of the present invention, there are provided methods of producing transgenic plants which are capable of bearing seedless fruits and/or pollenless flowers, or fruits and flowers which are substantially seedless and pollenless, respectively. These methods include the step of transforming a plant with a suitable expression system comprising the above-described nucleic acid sequences in altered form (e.g., mutated) to block, reduce or increase meiocyte formation in the plant. Persons of ordinary skill in the art can readily determine suitable expression systems. For example, genes under the control of a suitable promoter can be easily transformed in most crop plants by *Agrobacterium*-mediated and/or biolistic methods. See P. Christou, *Trends in Plant Science* 1:423–431.

Additional embodiments of methods of producing transgenic plants which are capable of bearing seedless fruits and/or pollenless flowers in a plant include the step of transforming a plant with the above-described nucleic acid sequences to block, reduce or increase meiocyte formation by using antisense and related techniques. Sense and antisense technology are routine methods to alter plant development and metabolism. For example, see Jorgensen, R. A. et al. *Plant Mol. Biol.* 31(5):957–73 (1996). The sense and antisense constructs can be introduced readily into plant cells by *Agrobacterium*-mediated and/or biolistic methods. See P. Christou, *Trends in Plant Science* 1:423–431.

In another embodiment, the present invention relates to methods of producing seedless fruits and/or pollenless flowers in a plant comprising the step of expressing in the plant the above-described nucleic acid sequences in altered form to affect meiocyte formation in the plant.

In a preferred embodiment of the present invention, the above-described method comprises the step of transforming a plant with an expression system comprising a nucleic acid or its complement involved in the formation of meiocytes, comprising: (a) nucleic acid encoding a protein according to FIG. 3 [SEQ ID NO:4], (b) a nucleic acid as set forth in FIG. 2 [SEQ ID NO:1], or a portion thereof, or (c) a nucleic acid as set forth in nucleotides 81–1024 of FIG. 2 [SEQ ID NO:1], or a portion thereof, wherein the nucleic acids are mutated to block, reduce or increase the formation of meiocytes in the plants, thereby rendering the plant capable of bearing seedless fruits or pollenless flowers.

In another embodiment of the present invention, there is provided a method of producing a plant capable of bearing seedless fruits or pollenless flowers, comprising the step of mutating endogenous DNA of the plant responsible for the formation of meiocytes, wherein the formation of meiocytes is affected and the plant becomes capable of producing seedless fruits or pollenless flowers, or fruits and flowers which are substantially seedless and pollenless, respectively. In a preferred embodiment of the invention, the endogenous DNA is mutated by direct mutagenesis. See. Mazzucato. A., et al., *Development* 125(1):107–114 (1998).

"Transgenic plants" include plants that contain endoqenous or exogenous DNA or RNA not occurring naturally in the wild type (native) plant or known variants, or contain additional or inverted copies of naturally-occurring DNA which is introduced as described herein, their progeny, whether produced from seeds, by vegetative propagation, cell, tissue or protoplast culture, or the like. Transgenic plants of the present invention may contain DNA encoding SPL protein or SPL-like proteins involved in meiocyte formation in the plant. For example, when introduced into and/or present in plant cells, the expression of SPL DNA or altered versions of SPL DNA may produce a plant lacking meiocytes or having more than the normal number of meiocytes found in untransformed plants of the same variety. For example, the maize macI mutant having an excess number of meiocytes causes complete male sterility and partial female sterility. The mechanism by which an excess of meiocytes results in sterility is currently unknown. See Sheridan, W. F., et al., *Genetics* 142:1009–1020 (1966).

The DNA in accordance with the present invention can be exogenous DNA added in a sense or antisense orientation and which encodes a protein involved in, and which may be required for, meiocyte formation in a plant. See Jorgensen, R. A., et al., *Plant Mol. Biol.* 31(5):957–73 (1996). The DNA of the present invention also can be exogenous DNA that has been altered (e.g., by mutation) so that it blocks, reduces or increases meiocyte formation. For example, the insertion of genetic elements, such as Ds sequences (with or without active Ac sequences) can affect meiocyte formation, and thus is of particular use in the present invention. The present invention further provides for direct or targeted mutagenesis of a plant's endogenous DNA responsible for meiocyte formation, which also can affect meiocyte formation.

Exogenous and endogenous DNA involved in meiocyte formation which have been mutated by direct mutagenesis differ from the corresponding wild type (naturally-occurring) DNA in that these sequences contain a substitution, deletion or addition of at least one nucleotide and can encode proteins which differ from the corresponding wild type protein by at least one amino acid residue. As used herein, the term "nucleotide" includes a residue of DNA or RNA.

Exogenous DNA, in altered or unaltered form, can be introduced into the target plant by well-known methods, such as *Agrobacterium*-mediated transformation, micro projectile bombardment, microinjection or electroporation. See, Wilkinson, J. Q., et al., *Nature Biotechnology* 15(5): 444–447 (1997).

Plant cells carrying exogenous SPL or SPL-like DNA, or endogenous SPL DNA mutated by direct mutagenesis, can be used to generate transgenic plants in which meiocyte formation is blocked, reduced or increased, and therefore be sources of additional plants, either through seed production or non-seed, asexual reproductive means (i.e., cuttings, tissue culture, and the like).

The present invention also provides plants, plant cells, and plant seed transformed with the above-described nucleic acid sequences. The formation of meiocytes can be affected in such transformed plants, plant cells, and plant seeds during meiocyte formation and during growth of plants.

In accordance with another embodiment of the present invention, there is provided a family of isolated proteins which can regulate or control the formation of meiocytes in male and female organs in plants. Such proteins include proteins that are functionally and structurally related to SPL and so are able to render a plant capable of bearing seedless fruits and/or pollenless flowers by interfering with the function of SPL. Such proteins also include related proteins from other plant species which are functional and structural equivalents of SPL in those species and perform the same function that SPL performs in *Arabidopsis*. An exemplary amino acid structure of the proteins of the present invention is set forth in FIG. 3 [SEQ ID NO:4]. The proteins of the present invention are involved in the formation of meiocytes in plants and comprise an amino acid sequence having at least about 80%, more preferably about 90% amino acid identity to the reference amino acid sequence in FIG. 3 [SEQ ID NO:4]; with greater than about 95% amino acid sequence identity being especially preferred. In a preferred embodiment, the invention provides proteins which comprise or have the same amino acid sequence as set forth in FIG. 3 [SEQ ID NO:4].

In accordance with another embodiment of the present invention, there are provided antibodies generated against the above-described proteins. Such antibodies may be employed in various applications, including to localize sites of regulatory activity in plants.

In another embodiment of the present invention, fusion proteins are provided which can comprise any of the above-described amino acids, and in a preferred embodiment, an SPL or SPL-type protein. The fusion proteins in accordance with the present invention also can comprise an additional peptide, such as a protein tag, which may be used to detect sites of SPL protein/protein interaction in plants.

In accordance with yet another embodiment of the invention, the nucleic acid molecules described herein (or fragments thereof) can be labeled with a readily detectable substituent and used as hybridization probes for assaying for the presence and/or amount of SPL or SPL-type DNA or RNA in a sample from a given plant species. In a preferred embodiment of the invention, isolated nucleic acid useful as a hybridization probe comprises a nucleic acid having a sequence of nucleotides as set forth in FIGS. 1A [SEQ ID NO:2] or 2 [SEQ ID NO:1], or a portion thereof. In a more preferred embodiment of the invention, the hybridization probe can be a nucleic acid comprising a nucleic acid having a sequence of nucleotides as set forth in nucleotides 81–1024 of FIG. 2 [SEQ ID NO:1], or a portion thereof. The nucleic acid molecules described herein, and fragments thereof, also are useful as primers and/or templates in a PCR reaction for amplifying genes encoding SPL protein or SPL-type proteins described herein.

Another embodiment of the invention provides an isolated promoter of the SPL gene. A fragment of DNA extending from 2690 nucleotides upstream of the start codon of the SPL gene has been identified as regulating expression of the SPL gene. The sequence of this promoter is shown in FIG. 5 [SEQ. ID NO: 18] as the sequence from base pair −2690 to −1 in the sequence. The first nucleotide of the start ATG codon is designated as position +1 in the sequence. The sequence from −2690 to −1 is sufficient to give SPL-specific expression in megasporocytes and microsporocytes. As used herein, "promoter" includes this sequence, a sequence which hybridizes to this sequence and promotes expression of a coding sequence operably linked thereto, and functional fragments of this sequence which are capable of promoting or regulating expression of a coding sequence operably linked thereto. The promoter can be operably linked to a coding sequence if it is linked to the ATG start codon of the coding sequence.

The promoter of the SPL gene can be used to drive expression of the SPL gene or of a foreign gene in microsporocytes and megasporocytes of plants One utility of the promoter is to permit expression of transgenes specifically in the reproductive cells of the plant. If a transgene, such as a gene encoding a ribonuclease, is expressed under the control of the SPL promoter, the plants will be rendered sterile. Alternatively, the SPL promoter can be used to express genes encoding transposases or recombinases (proteins that catalyze DNA rearrangements) specifically in reproductive cells (sporocytes), such that the next generation of seeds will have an altered DNA structure from the parent plant. For example, a plant carrying a Cre recombinase under the control of the SPL promoter can be used to excise segments of transgenic DNA specifically from the sporocytes. As a result, the parent plant will carry the transgenes, but the progeny will lack the transgene. This result is helpful when it is desired to prevent the spread of transgenes from one generation to the next.

The following studies were conducted in connection with the present invention and are not to be construed as limiting the scope of the present invention.

Mutations in the recessive spl gene were identified during screening of gene trap lines in *Arabidopsis thaliana* ecotype landsberg erecta. From a finding that these mutations caused male and female sterility in the plant, it was concluded that the SPL gene plays a pivotal role in plant reproduction. The spl homozygous plants also exhibited an overall morphology that was similar to the morphology of wild type plants, except for a delay in senescence in the spl homozygous plants. Additionally, the flowers of the spl homozygous plants were found to have a normal number of organs, as in the wild type plants, except that the flowers of the spl homozygous plants included white, flat anthers and lacked visible pollen grains at anthesis in stage 13–14. See D. R. Smyth, J. H. Bowman, E. M. Meyerowitz, 1990, *Plant Cell* 2, 755. The carpel of these spl homozygous plants also appeared morphologically normal, although being infertile when pollinated with wild type pollen grains.

Cytological studies using whole mount clearing and sectioning techniques demonstrated that meiocyte formation was affected in both anther and carpel of the spl homozygous plants. Studies of the spl homozygous plants also revealed that in spl mutant flowers the hypodermal cell of the anther enlarged slightly in stage 7 and differentiated into an archesporial cell, as occurs normally in wild type flowers. The archesporial cell then differentiated and sometimes divided periclinally to form the PPC layer and the PSC layer. The PPC layer occasionally divided an additional time to produce two secondary parietal cell layers that ceased dividing. However, cells closer to the center of the anther became vacuolated, and the development of microsporocytes and tapetum was not observed. Additionally, at anthesis in stages 13–14, the anthers were composed of highly vacuolated parenchymatous cells, and in some cases, several vascular cells also were present.

In contrast, the results of the above studies differed from those of the wild type *Arabidopsis* in which the wild type was found to exhibit microsporogenesis as typically exhibited by dicotyledonous plants. Specifically, in immature flowers at stage 7, a single hypodermal cell at each corner of the anther locules expanded radially and differentiated into an archesporial cell. The archesporial cell underwent a periclinal division, resulting in an inner primary sporogenous cell (PSC) layer and an outer primary parietal cell (PPC) layer. The PPC layer subsequently divided periclinally and anticlinally to form two secondary parietal cell (SPC) layers, while the inner SPC layer differentiated into the tapetum. The outer SPC layer then divided periclinally an additional time to form two more layers called the endothecium, which lies outside, and the middle layer, which lies inside. None of these layers that are descended from the PPC or primary parietal cell layer have any direct role in spore formation, although they are important for maturation of the pollen grains. The spores were formed from the cells of the PSC layer (primary sporogenous layer)

which differentiated directly into microsporocytes (male meiocytes), also referred to as pollen mother cells (PMCs) in late stage 8 flowers. During stage 9, the PMCs separated from one another by the deposition of callose on the cell wall, and subsequently underwent meiosis. See Bowman, J., 1994, *Arabidopsis, An Atlas of Morphology and Development*. At the same time, the tapetum became visible and appeared binucleate due to endomitosis.

It was concluded from the above studies with the spl mutant in comparison to the wild type plants that microsporogenesis in spl mutant plants is blocked during the transition from the PSC layer to microsporocytes, resulting in a phenotype lacking any microsporocytes.

In the spl mutants studied in accordance with the present invention it also was found that the ovule primordia formed normally, and the top hypodermal cell increased slightly in size. The archesporial cell was formed as in the wild type plant, but was unable to elongate longitudinally to develop into megasporocyte or female meiocyte. Therefore, the spl mutant failed to form megasporocyte, and as a result, the nucellus became arrested. However, both inner and outer integuments differentiated normally as in wild flower type flowers. The endothelium also differentiated from the inner cell layer of the inner integument. Shortly after the integument developed in stage 13 flowers, the top epidermal cell of the arrested nucellus elongated and started to divide transversely and mitotically, and thereafter the two neighboring epidermal cells also divided transversely. As a result, the nucellus grew towards the micropyle to produce a three layered finger-like structure on a longitudinal section of the ovule in and after stage 14 flowers.

The spl mutation prevented the transition from the archesporial cell to megasporocyte during megasporogenesis, which was evidenced in part by the absence of callose deposition on carpel at different flower stages, as observed during wholemount staining with aniline blue. However, this did not affect the development of sporophytic tissues such as integument, thus indicating that the spl mutation specifically blocked the transition from the archesporial cell into megasporocyte in the plant.

The SPL gene product thus appears to play a pivotal role in the formation of microsporocytes in the male plant and megasporocytes in the female plants. Genetic studies, including Southern blot analysis using the 5' Ds sequence as probe, showed that the spl sterile phenotype was caused by a single Ds insertion. Additional reversion experiments confirmed that the spl mutant gene is tagged by the Ds element. Excision of this Ds element by the Ac transposase gene restored sporocyte formation and normal fertility. In these experiments, ten independent revertant plants, which were fully fertile, were isolated. In each instance, it was determined that the Ds element within the SPL gene had undergone precise excision, restoring the wild-type sequence and function.

Genomic sequences flanking the Ds element were detected by using the thermal asymmetric interlaced-PCR (TAIL PCR) technique, as described by Liu, et al., *The Plant J.*, 8:457 (1995) As shown in FIGS. 1A and 1B [SEQ ID NOS:2 and 3], fragments immediately flanking each of the 3' and 5' ends of the Ds element were sequenced and found to contain, as expected, the 3' and 5' portions of the Ds sequence. The above PCR fragments were used as a probe to screen a cDNA library from *Arabidopsis thaliana* Landsberg erecta flower. A cDNA clone of the SPL gene was isolated and sequenced. As shown in FIG. 2 [SEQ ID NO:1], the full-length cDNA clone was found to be 1302 bp in length and to encode a 314 amino acid polypeptide having a molecular weight of 34 kDa, as shown in FIG. 3 [SEQ ID NO:4].

Additionally, searches of databases of protein sequences revealed that the SPL protein, as shown in FIG. 3 [SEQ ID NO:4], was not homologous to any known proteins, thus confirming the novelty of the SPL protein. Partial homologies to amino acid regions of known proteins are by three short regions of the SPL protein. Specifically, one 33 amino acid domain from positions 149 to 181 of the SPL protein was found to be homologous to an amino acid region of *Sacchromyces cerevisiae* SWE1, a mitosis inhibitor, with 45% identity. Another 15 amino acid region from positions 119 to 133 of the SPL protein was found to be homologous, with 73% identity, to an amino acid region of 3-hydroxyisobutyrate dehydrogenase precursor from rat. However, both of the above amino acid regions are from unrelated proteins and have an unknown function.

In addition, there is a predicted helix region in SPL protein from amino acids 64 to 85 that has limited homology with the first helix region of the protein motif called the MADS domain that binds DNA. The MADS domain is a highly conserved region of about 57 amino acids found in a family of transcription factors called MADS box factors (See, e.g., Kramer et al., *Genetics* 149:765–783 (1998)). SPL does not have the entire MADS domain, but it shows good conservation to the first 18 amino acids of this domain. A comparison of amino acids 64 to 80 of SPL with the first amino acids of the MADS domain from known regulatory proteins of this class from a variety of species is shown in FIG. 4 [SEQ ID NOS:5–17].

As shown in FIG. 4 [SEQ ID NOS:5–17], the MADS box transcription factors listed are the AP3, AG, AGL5 and AGL11 proteins of *Arabidopsis*; DEFA and GLO proteins of *Antirrhinum* (snapdragon); BOAP1 from *Brassica oleracea*; FBP11 from *petunia*; MCM1, RLM1, SMP1 proteins from budding yeast; and SRF and MEF2D human proteins.

The nuclear localization of SPL and its partial homology with the previously described MADS domain proteins suggest that SPL may represent a new class of transcription regulatory protein.

Northern blot analysis of polyA$^+$ RNAs from flowers, roots, leaves, stems and silique of *Arabidopsis* using the above-described cDNA clone as a probe revealed a 1.3 kb band only in RNA extracted from the flower, thus suggesting that the SPL gene is expressed differently in different plant tissues. In situ hybridization using as the probe labeled antisense RNA, synthesized from the SPL cDNA clone, also demonstrated that the SPL gene is expressed in sporogenous cells in flowers, which is consistent with the biological function of the gene.

As shown in FIGS. 1A, 1B [SEQ ID NOS:2 and 3] and 2 [SEQ ID NO:1], a comparison of genomic sequences with a cDNA sequence from *Arabidopsis* revealed that the Ds element is inserted between bases 411 and 412 of the SPL gene. This insertion of the Ds element caused a 4 bp duplication of the host sequence at the insertion site. Sequences obtained from more than 10 independent reversion lines revealed a perfect excision, and no footprints, thus indicating the importance of the region comprising the amino acids immediately flanking the insertion site to the function of the SPL gene. this conclusion was based upon the observation that all revertants of the spl mutation were precise excisions of the Ds element. When a Ds element is inserted into a gene, there typically are revertants in which there are small deletions, substitutions or insertions of one or two amino acids (Wessler, S. R., *Science* 242(4877): 399–405 (Oct. 21, 1988)). That no such revertants were recovered from the spl mutation is evidence that even small changes in the amino acid sequence at the site of insertion are deleterious to the function of the SPL protein.

Southern hybridization analysis showed that the SPL gene is a single gene.

In accordance with the present invention, the Sporocyteless (SPL) gene from *Arabidopsis thaliana* thus appears to play an important, if not essential, role in the transition from archesporial cells to meiocytes in both male and female organs of plants. As stated above, sporogenesis is a key step in the reproduction of a plant, and thus the ability of a plant to control sporogenesis also affects the plant's ability to yield seeds. The genetic studies of the spl mutation of *Arabidopsis* described herein show that the SPL gene encodes a protein that is important, if not essential, for meiocyte formation. Using transposon tagging, the SPL gene was isolated and characterized. Additional Southern analysis under moderate stringency levels should reveal SPL homologues in other plant species, such as maize and rice, having the same or similar function as the SPL gene.

As stated above, the isolated DNA provided by this invention may be used as a probe to isolate in other plant species DNA sequences that are homologous to the SPL gene and encode regulatory proteins which are involved in meiocyte formation in the same or similar way as is protein encoded by the SPL gene. As stated above, the terms "homology" and "homologous" in the present invention mean an overall sequence identity of at least 50%. The identification and isolation of SPL-type genes (i.e., homologues of the SPL gene) of other plant species may be carried out according to standard methods and procedures known to those skilled in the art. See, e.g., Sambrook, et al. *Molecular Cloning, A Laboratory Manual*, Cold Spring Harbor Laboratory Press, Cold Spring Harbor, N.Y. (1989).

By using these and other similar techniques, those skilled in the art can readily isolate not only the SPL gene from different cells and tissues of *Arabidopsis*, but also homologues of the SPL gene from other plant species. For example, SPL or SPL-type genes in other plant species may be identified and isolated by preparing a genomic and/or cDNA library of the plant species, followed by probing either or both of the libraries with all or a portion of either of the sequences shown in FIGS. 1A [SEQ ID NO:2] and 2 [SEQ ID NO:1], or their homologues, identifying the hybridized sequences, and isolating the hybridized DNA to obtain the SPL or SPL-type gene. Once identified, these SPL or SPL-type genes from other plant species may be restriction mapped, sequenced and cloned.

The isolated SPL gene, or a homologue thereof, also may be altered and thereafter introduced into *Arabidopsis* or another plant species to regulate and control meiocyte formation to produce seedless fruits and/or pollenless plants. For example, an engineered SPL gene may be incorporated into a plant line, which has been bred for other traits, to produce seedless fruits.

Meiocyte formation also can be blocked by decreasing the expression levels of SPL protein by using antisense constructs or co-suppression of the SPL gene. Alternatively, by placing the sense or antisense SPL gene under the control of different inducible promoters, meiocyte formation also can be controlled, subject to specific environmental conditions or applied chemicals.

"Cosuppression" refers to the over-expression of an endogenous or introduced exogenous gene (transgene), wherein the extra copies of the gene cause coordinate silencing of both the endogenous gene and transgene, thus reducing or eliminating expression of a certain trait. See, e.g., U.S. Pat. Nos. 5,034,323 and 5,283,184. The transgene can be introduced in a sense or antisense orientation and does not require a full-length sequence or absolute homology to the endogenous sequence intended to be repressed.

Furthermore, a dominant-negative mutant of the SPL protein can be constructed by using a truncated version of the SPL gene that is able to interact with its partners, but is unable to fulfill its biological activity. See Wilkinson, J. Q., et al., *Nature Biotechnology* 15(5):444–447 (1997). If this truncated gene is introduced into a plant under the control of a strong promoter, the transgenic plant should reduce or lose its ability to form seeds. Therefore, a truncated dominant-negative SPL gene could act as a substitute for the antisense SPL gene. The dominant-negative SPL gene approach also has advantages over the antisense construct when engineering seedless or pollenless plants, including that the antisense strategy depends on initially cloning part or all of the SPL gene from each plant species, followed by expressing the gene in an inverted orientation. Antisense suppression also is dependent on the expression of the complementary nucleotide sequences, which vary from one species to another. In contrast, the dominant-negative strategy is dependent only on the functional conservation of the protein and its target sites, which is a much less stringent requirement overall than is nucleotide sequence conservation. There are several examples of regulatory proteins that can perform a similar function when expressed in widely divergent species of plants, as discussed in Lloyd, A. M. et al., (1992), *Science* 258: 1773–1775; Irish, V. F. and Yamamoto, Y. T., (1995), *Planet Cell* 7: 1635–1644. This type of functional conservation suggests that the dominant-negative version of the *Arabidopsis* SPL gene also can work similarly in other planet species.

The following examples describe specific aspects of the invention to illustrate the invention and describe methods for isolating and identifying the SPL gene. The examples should not be construed as limiting the invention in any way.

All citations in this application, including those to materials and methods, are hereby incorporated by reference.

EXAMPLE 1

Transposon Tagging

Plants were grown at 22° C. under 16 hr light/8 hr dark cycle in green houses at the Institute of Molecular Agrobiology, 1 Research Link, Singapore. Starter lines containing Ds or Ac segments were crossed and screened for transposants of F2 seeds, according to Sundaresan, V., et al., 1995, *Genes & Development*, 9:1797–1810. The spl mutant gene was identified from among a collection of transposants by its male and female sterile phenotypes. Genetic analysis was carried out using techniques recognized in the art. The spl mutant gene was shown to be recessive and caused by a single Ds insertion. The phenotype of the spl mutant gene was characterized by standard cytological methods, as discussed, for example, in O'Brien, T. P. and McCully, M. E., 1981, *The Study of Plant Structure: Principles and Selected Methods*, Termarcarphi, Melbourne; and by whole-mount clear methods, as discussed in Herr, J. J. M., 1982, *Stain Technol.* 57: 161–169.

EXAMPLE 2

DNA Analysis

DNA analysis procedures were performed primarily as described in Sambrook, J., et al., 1989, *Molecular Cloning: A Laboratory Manual*, Cold Spring Harbor Laboratory Press, Cold Spring Harbor Laboratory, New York.

For Southern blot analysis, 100–200 ng *Arabidopsis* DNA was extracted from flower buds and digested with EcoRI, HindIII, or XbaI and electrophoresed on a 1% agarose gel prior to transfer to a nylon membrane. The Ds probe, an EcoRI fragment from the 5' end of the gene trap construct, DsG (see V. Sundaresan et al., *Genes & Development* 9:1797–1810 (1995)), was prepared by digesting the plasmid pWS31, which contained parts of Ds elements, with EcoRI and separating the resulting fragments by gel electrophoresis. A 1.8 kb EcoRI fragment of a 5' Ds element was cut from the gel and labeled with $^{32}$P-dCTP, using the Rediprime kit from Amersham. The labeled fragment was used to probe Southern blots under standard DNA hybridization conditions.

To isolate the DNA immediately flanking the Ds element, about 10 ng DNA from flower buds was used for TAIL PCR (Liu, et al., 1995, *The Plant J.* 8, 457). The amplified fragments were isolated by gel electrophoresis and sequenced. The PCR fragments were labeled with $^{32}$P-dCTP and used to screen a flower cDNA library. Phages in the library that hybridized to the PCR fragments were purified, and plasmid DNA was excised in vitro according to a standard protocol. The size of the insert was determined by digesting the plasmid with the restriction enzymes EcoRI and KpnI, both available from Stratagene.

EXAMPLE 3

RNA Analysis

Northern blot analysis of polyA+ RNA from various *Arabidopsis* tissues was performed using a 1 kb HindIII fragment of the cDNA clone of FIG. 2 [SEQ ID NO:1] as a probe. RNA was extracted from different tissues using standard methods. 10 µg polyA+ RNA from each sample was electrophoresed on 1% agarose gel and transferred to a nylon membrane. The membrane was then hybridized with a $^{32}$P-dCTP labeled probe.

EXAMPLE 4

Sequence of the SPL Gene

The SPL cDNA clone of FIG. 2 [SEQ ID NO:1] was sequenced using the dideoxy method with fluorescent labeled terminators. T3 and T7 oligonucleotide primers, which hybridized to the plasmid vector containing the SPL cDNA, were used to generate initial sequences from the ends of the clone. Additional primers within the SPL gene, based on the above sequences, were then designed and used to sequence the central region of the SPL gene. Approximately 600–700 bp of the clone could be read from each primer.

EXAMPLE 5

In Situ Localization of the SPL mRNA

Flower buds were fixed with FAA for 20 hours at 4° C., dehydrated with ethanol and made transparent with xylene. The tissues were embedded in paraplast and 7–101 µm thick sections were made. The sections were then deparaffinized with xylene and processed for in situ hybridization. To obtain sense RNA probe, the plasmid containing the SPL cDNA was linearized with KpnI and transcribed with T3 RNA polymerase in the presence of DIG-UTP. For antisense RNA probe, the plasmid was cut with BamHI and transcribed in the presence of DIG-UTP with T7 RNA polymerase. The lengths of the probes were reduced by alkaline treatment to a fragment having a length of about 150 bp. Hybridization was performed according to a standard protocol. See Jackson, D., 1991, In situ Hybridization in Plants, in *Plant Pathology: A Practical Approach*, Oxford University Press.

EXAMPLE 6

Determination that SPL Protein is a Nuclear Protein

It has been determined that the SPL protein is a nuclear protein. A translational fusion of the SPL protein to the GUS reporter gene (Jefferson, R. A., *Nature* 342(6251):837–8 (December, 1989) was utilized for this purpose. The method used for determining the nuclear localization has been previously described for other proteins (e.g., Pepper et al., *Cell* 78(1):109–116 (1994)).

Two primers, SPL-Xba-S:5'CTAGTCTAGTCTAG-AAGATCATCA3' [SEQ ID NO:19] and SPL-BamHI-T:5'CGGATCCAAGCTTCAAGGACAAATCAATGGT3' [SEQ ID NO:20], which introduced restriction enzyme sites immediately upstream of the SPL start codon and the SPL stop codon, respectively, were used to amplify the complete SPL coding sequence from the cDNA. This amplified fragment was cloned in front of the GUS gene in the pBI221 vector (Clontech), giving rise to clone pBI221-SPL, which encodes a SPL-GUS fusion. The gene fusion in pBI221-SPL is driven by the 35S promoter and will result in the synthesis in plant cells of a fusion protein consisting of the complete SPL protein at the N terminus and the GUS protein at the C terminus.

The pBI221-SPL plasmid DNA was introduced into onion epidermal cells using the BioRad PDS-1000/He particle bombardment system. The samples were kept overnight at room temperature and stained with X-Gluc, a histochemical stain for GUS activity (Jefferson, R. A., *Nature* 14:342 (6251):837–8 (December, 1989)). The SPL-GUS fusion protein was found to be localized exclusively in the nucleus, whereas in the same experiment a control GUS protein with no fusion was localized to the cytoplasm. This experiment demonstrates that SPL is a nuclear protein, which is consistent with its proposed function as a regulatory protein required for sporocyte development.

EXAMPLE 7

Promoter of the SPL Gene

A fragment of DNA from 2690 nucleotides upstream of the start codon of the SPL gene was fused to a promoterless GUS gene in a binary T-DNA vector designated pZIP111 (Hajdukiewicz, P., et al., *Plant Mol. Biol.* 25:989–994 (1994) for plant transformation. The SPL promoter-GUS co-construct was introduced into Landsberg plants by vacuum infiltration and transformed plants were selected by standard methods (e.g., Bechtold, N., and Pelletier, G., *Methods Mol. biol.* 82:259–266 (1998)). A histochemical staining procedure was used to monitor expression of the GUS reporter gene (Jefferson, R. A., *Nature* 342(6251): 837–8 (December, 1989)). The transgenic plants showed expression of the GUS reported gene in the megasporocytes and microsporocytes. The pattern of GUS expression observed was similar to the expression pattern of the SPL gene, as determined by in situ localization of SPL RNA (see Example 5, above). This experiment showed that the 2690 base pairs of DNA upstream of the SPL start codon contain the SPL promoter region, and that this sequence of DNA was sufficient to confer the specificity of expression of the SPL gene (i.e., expression in sporocytes) to a heterologous transgene such as the GUS gene.

While the invention has been described in detail with reference to certain preferred embodiments thereof, it will be understood that modifications and variations are within the spirit and scope of that which is described and claimed.

What is claimed is:

1. An isolated nucleic acid or its complement comprising nucleic acid encoding a protein comprising SEQ ID NO: 4.

2. An isolated nucleic acid or its complement according to claim 1, wherein said nucleic acid comprises the nucleic acid as set forth in SEQ ID NO: 1.

3. An isolated nucleic acid or its complement according to claim 2, wherein said nucleic acid comprises the nucleic acid as set forth in nucleotides 80–1024 of SEQ ID NO: 1.

4. A plant cell transformed with an isolated nucleic acid sequence or its complement comprising nucleic acid encoding a protein comprising (a) the amino acid sequence as set forth in SEQ ID NO: 4, or (b) an amino acid sequence having at least 95% sequence identity with the amino acid sequence set forth in SEQ ID NO: 4 and which is involved in meiocyte formation in a plant.

5. The plant cell of claim 4, wherein said isolated nucleic acid comprises SEQ ID NO: 1.

6. The A plant cell of claim 5, wherein said isolated nucleic acid comprises nucleotides 80–1024 of SEQ ID NO: 1.

7. An isolated nucleic acid encoding a protein involved in meiocyte formation in a plant, wherein said protein comprises:

(a) the same amino acid sequence as set forth in SEQ ID NO: 4, or (b) an amino acid sequence having greater than about 95% sequence identity to the amino acid sequence set forth in SEQ ID NO:4 and which is involved in meiocyte formation in a plant.

8. An isolated nucleic acid or its complement, wherein said nucleic acid comprises naturally occurring DNA, or DNA degenerate to said naturally occurring DNA from a plant, having at least about 95%–98% identity to SEQ ID NO:1, and wherein said nucleic acid encodes a protein which participates in meiocyte formation in a plant.

9. An isolated nucleic acid or its complement, wherein said nucleic acid comprises naturally occurring DNA, or DNA degenerate to said naturally occurring DNA from a plant, having at least about 95%–98% identity to nucleotides 80–1024 of SEQ ID NO:1, and wherein said nucleic acid encodes a protein which participates in meiocyte formation in a plant.

10. The isolated nucleic acid of claim 7, wherein said plant is *Arabidopsis*.

* * * * *